(12) United States Patent  
Hsu et al.

(10) Patent No.: US 9,399,117 B2  
(45) Date of Patent: Jul. 26, 2016

(54) SYSTEMS AND METHODS FOR PROVIDING SECUREMENT AND POSITION VERIFICATION FOR MEDICAL CATHETERS

(71) Applicants: George Hsu, Evans, GA (US); Xiaoyu Alan Zheng, Germantown, MD (US)

(72) Inventors: George Hsu, Evans, GA (US); Xiaoyu Alan Zheng, Germantown, MD (US)

(*) Notice: Subject to any disclaimer, the term of this patent is extended or adjusted under 35 U.S.C. 154(b) by 0 days.

(21) Appl. No.: 14/934,249

(22) Filed: Nov. 6, 2015

(65) Prior Publication Data

US 2016/0136395 A1 May 19, 2016

Related U.S. Application Data

(63) Continuation of application No. 14/818,246, filed on Aug. 4, 2015.

(60) Provisional application No. 62/136,721, filed on Mar. 23, 2015, provisional application No. 62/079,405, filed on Nov. 13, 2014.

(51) Int. Cl.
*A61M 25/02* (2006.01)
*A61M 5/50* (2006.01)
*A61M 25/00* (2006.01)

(52) U.S. Cl.
CPC .............. *A61M 25/02* (2013.01); *A61M 5/5086* (2013.01); *A61M 2025/0008* (2013.01); *A61M 2025/024* (2013.01); *A61M 2025/0273* (2013.01)

(58) Field of Classification Search
CPC ..................... A61M 25/02; A61M 2025/0246; A61M 2025/024; A61M 2025/0266; A61M 2025/026; A61M 2025/028; A61M 2025/0206; A61M 25/01; A61M 25/013; A61M 2025/0008; A61M 2025/0273; A61M 5/5086; A61M 2205/3306

See application file for complete search history.

(56) References Cited

U.S. PATENT DOCUMENTS

| | | | |
|---|---|---|---|
| 4,699,616 A | 10/1987 | Nowak et al. | |
| 4,898,587 A | 2/1990 | Mera | |
| 4,976,698 A | 12/1990 | Stokley | |
| 5,068,886 A | 11/1991 | Lavia | |
| 5,267,967 A | 12/1993 | Schneider | |
| 5,456,671 A | 10/1995 | Bierman | |
| 5,707,363 A | 1/1998 | Crawford et al. | |
| 6,387,076 B1 | 5/2002 | Landuyt | |
| 6,458,104 B2 | 10/2002 | Gautsche | |
| 7,025,748 B2 | 4/2006 | Ashby | |
| 7,618,400 B2 | 11/2009 | Chawki | |
| 7,776,017 B2 | 8/2010 | Ponzi et al. | |
| 8,142,401 B2 | 3/2012 | Rosenberg | |
| 8,265,732 B2 | 9/2012 | Besz et al. | |
| 8,439,873 B1 | 5/2013 | Donovan | |
| 8,556,859 B2 | 10/2013 | Nilson et al. | |
| 8,608,727 B2 | 12/2013 | Michels et al. | |
| 8,740,847 B2 | 6/2014 | Levesque et al. | |

(Continued)

*Primary Examiner* — Bhisma Mehta
*Assistant Examiner* — Brandy S Lee
(74) *Attorney, Agent, or Firm* — McClure, Qualey & Rodack, LLP

(57) ABSTRACT

An antimicrobial, securement, and position verification device for medical catheters is disclosed. A film, medical grade adhesive, and antimicrobial substance disposed on the medical grade adhesive operate in conjunction to secure the device to the patient's skin and to prevent infections. The catheter is secured by guide channels in the foundation and securement cover through the use of one or more adhesives impregnated with antimicrobial substances. The device further comprises catheter position alert media and indicators configured to indicate any unintentional positional changes.

9 Claims, 11 Drawing Sheets

(56) References Cited

U.S. PATENT DOCUMENTS

| | | |
|---|---|---|
| 2005/0070794 A1 | 3/2005 | Deal et al. |
| 2005/0101933 A1* | 5/2005 | Marrs .................. A61M 5/158 604/506 |
| 2005/0215953 A1 | 9/2005 | Rossen |
| 2007/0043326 A1* | 2/2007 | Navarro ................ A61M 25/02 604/264 |
| 2007/0149924 A1* | 6/2007 | Marsh .................. A61M 5/002 604/117 |
| 2008/0132848 A1 | 6/2008 | Wright et al. |
| 2010/0016801 A1 | 1/2010 | Rosenberg et al. |
| 2012/0041378 A1 | 2/2012 | Bierman |
| 2012/0046533 A1 | 2/2012 | Voskanyan et al. |
| 2012/0109070 A1 | 5/2012 | Elsamahy et al. |
| 2012/0259221 A1 | 10/2012 | Sheldon et al. |
| 2013/0079721 A1 | 3/2013 | Mizoguchi et al. |
| 2014/0066882 A1 | 3/2014 | Heinecke et al. |
| 2014/0074031 A1* | 3/2014 | Bornhoft ............... A61M 39/10 604/164.01 |
| 2014/0128814 A1 | 5/2014 | Peterson et al. |
| 2014/0148788 A1 | 5/2014 | Ryan et al. |
| 2014/0163515 A1 | 6/2014 | Hyman et al. |
| 2014/0200517 A1 | 7/2014 | Humphries et al. |
| 2014/0228810 A1 | 8/2014 | Rosenberg |
| 2014/0323967 A1 | 10/2014 | Mancino |

\* cited by examiner

SYSTEMS AND METHODS FOR PROVIDING SECUREMENT AND POSITION VERIFICATION FOR MEDICAL CATHETERS

CROSS-REFERENCE TO RELATED APPLICATION

This application is a continuation of application Ser. No. 14/818,246 entitled "Systems and Methods for Providing Securement and Position Verification for Medical Catheters" filed on Aug. 4, 2015, which claims priority to, and the benefit of, U.S. Provisional Patent Application entitled, "Antimicrobial, Securement, and Position Verification Device for Medical Catheters," having Ser. No. 62/136,721, filed on Mar. 23, 2015 and U.S. Provisional Patent Application entitled, "Antimicrobial, Securement, and Position Verification Device for Medical Catheters," having Ser. No. 62/079,405, filed on Nov. 13, 2014, which are incorporated by reference in their entireties.

TECHNICAL FIELD

The present disclosure generally relates to medical devices and more particularly, to an antimicrobial, securement, and position verification device for medical catheters.

BACKGROUND

Medical catheters are invaluable tools in the medical field, but their use is not without problems. Catheter associated infections and inadvertent positional shifts are a major source of morbidity and mortality for patients. Healthcare providers are also unable to assess positional changes in catheters without utilizing radiographic imaging. This exposes the patient to unnecessary radiation and is also financially costly. While devices exist that individually address catheter associated problems, the use of multiple devices is cumbersome and inefficient in the healthcare process.

SUMMARY

Briefly described, one embodiment, among others, is a device for securing and monitoring movement of a medical catheter, comprising a film having an adhesive on a body-facing surface for securing the film to a body, the adhesive having antimicrobial properties. The device further comprises a securement foundation mounted on the film, a securement cover, and a hinge member coupling the securement foundation to the securement cover, wherein when the securement cover and the securement foundation are configured in a closed state via the hinge, the securement cover and the securement foundation form a housing with a guide channel for securing the catheter.

Another embodiment is a method for securing and monitoring movement by a medical catheter. The method comprises inserting the medical catheter into the body and threading the medical catheter through an opening in a film having an adhesive disposed on a body-facing surface, the adhesive having antimicrobial properties. The method further comprises attaching the film to the body via the adhesive and placing the catheter in a guide channel formed by a securement foundation mounted on the film and a securement cover, the securement foundation being coupled to the securement cover via a hinge.

Another embodiment is a device for securing and monitoring movement of a medical catheter, comprising a film having an adhesive disposed on a body-facing surface for securing the film to a body, the adhesive having antimicrobial properties. The device further comprises a securement foundation mounted on the film, a securement cover, and a hinge member coupling the securement foundation to the securement cover, wherein when the securement cover and the securement foundation are configured in a closed state via the hinge, and wherein the securement cover and the securement foundation form a housing with a guide channel for securing the catheter, the guide channel having approximately a same diameter as a diameter of the medical catheter, the guide channel having an adhesive disposed thereon for restricting movement of the medical catheter. The device further comprises a catheter entry point extending from a center of the device through the housing to an edge of the film.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Medical catheters are invaluable tools in the medical field, but their use is not without problems. Typically, upon initial placement of a catheter, the healthcare provider applies an adjuvant antimicrobial barrier device at the site of catheter insertion. A secondary adjuvant device is then applied over the medical catheter to secure the catheter position. Significantly, the use of multiple adjuvant devices in conjunction with a medical catheter is inefficient and increases the risk of malfunction and subsequent harm to the patient. Furthermore, healthcare providers are unable to assess positional shifts of a medical catheter without utilizing a radiographic study, which is expensive and exposes the patient to unnecessary radiation.

Various embodiments are described for incorporating an antimicrobial, securement, and position verification device utilized in conjunction with medical catheters. By utilizing the device disclosed herein, healthcare providers are able to address the problems of catheter associated infections, catheter securement, and detection of inadvertent catheter positional shifts in a single device, thereby simplifying the utilization of a medical catheter.

In accordance with various embodiments, the device is configured as a single adjuvant to medical catheters and attaches at the entry point of the catheter to the skin. For some embodiments, the device fully covers the catheter entry site while clamping down on the body of the catheter to prevent any positional shifts. Indicators are implemented on the device, which alert healthcare providers of any positional shifts by the catheter that may have occurred. Notably, a single device is disclosed that provides antimicrobial protection, securement against positional shifts, and the ability to alert healthcare providers of inadvertent positional shifts without the need for additional radiographic studies.

Figure 1:
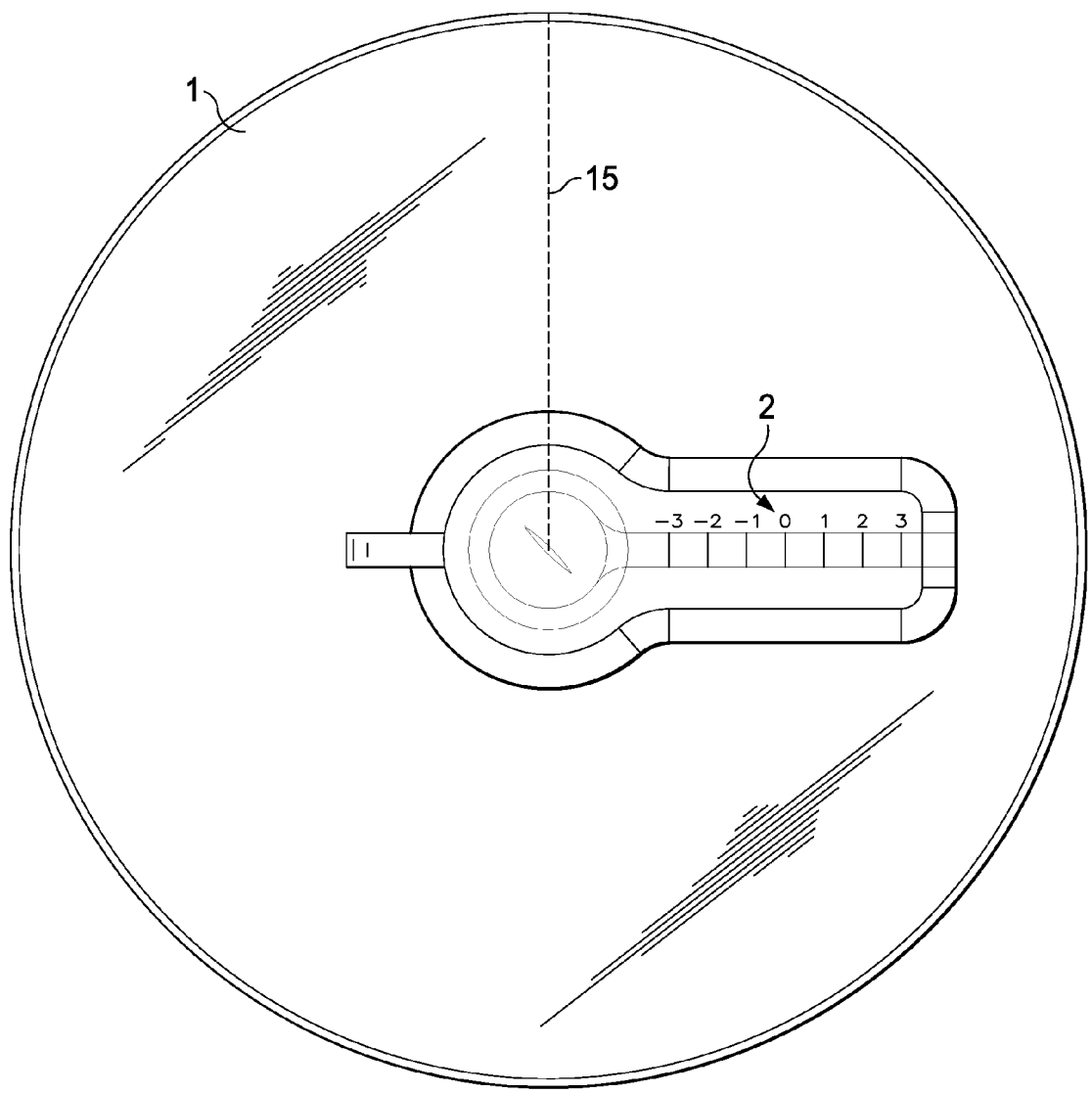
FIG. 1 illustrates a top view of the device in accordance with various embodiments.
Figure 2:
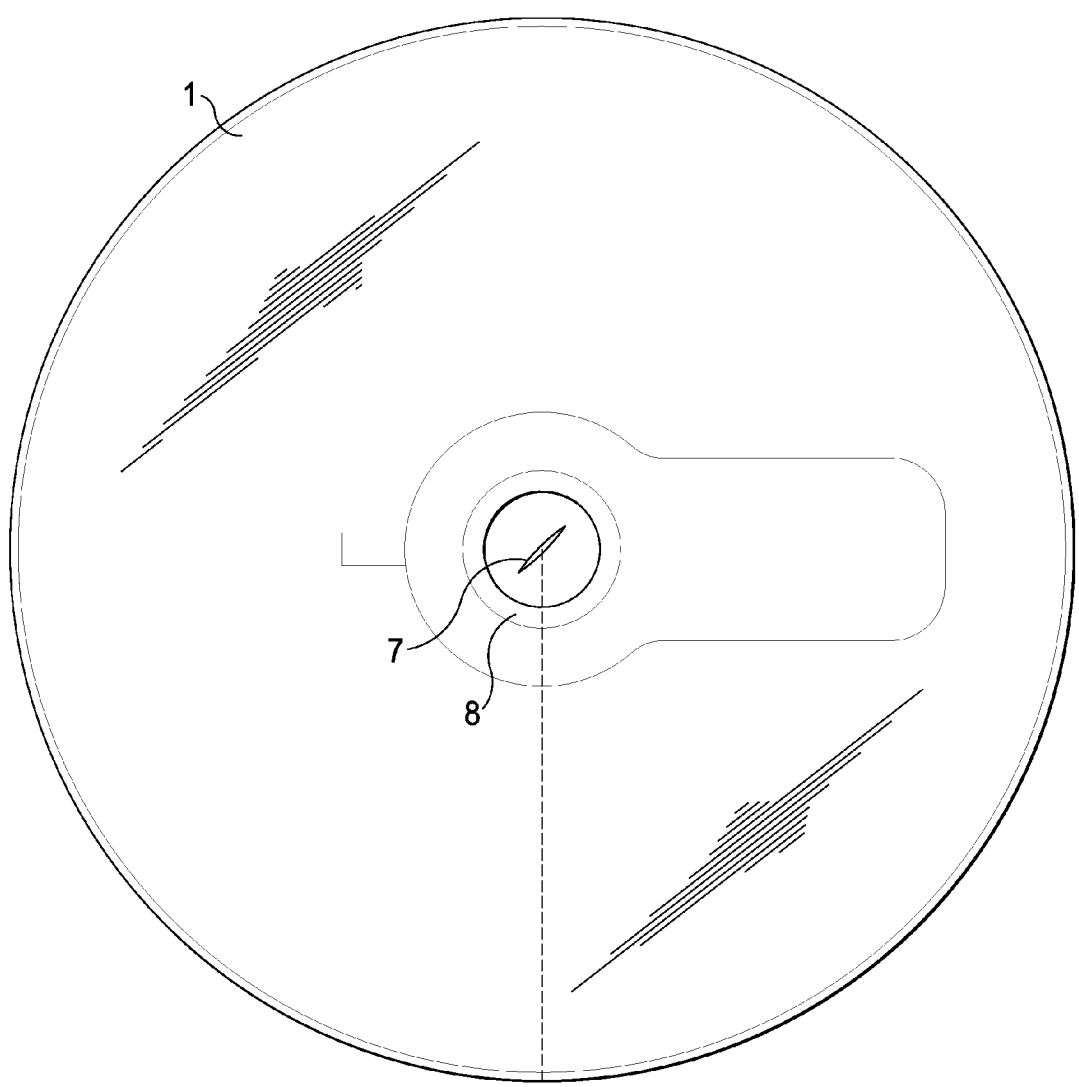
FIG. 2 illustrates a bottom view of the device in accordance with various embodiments.
Figure 3:
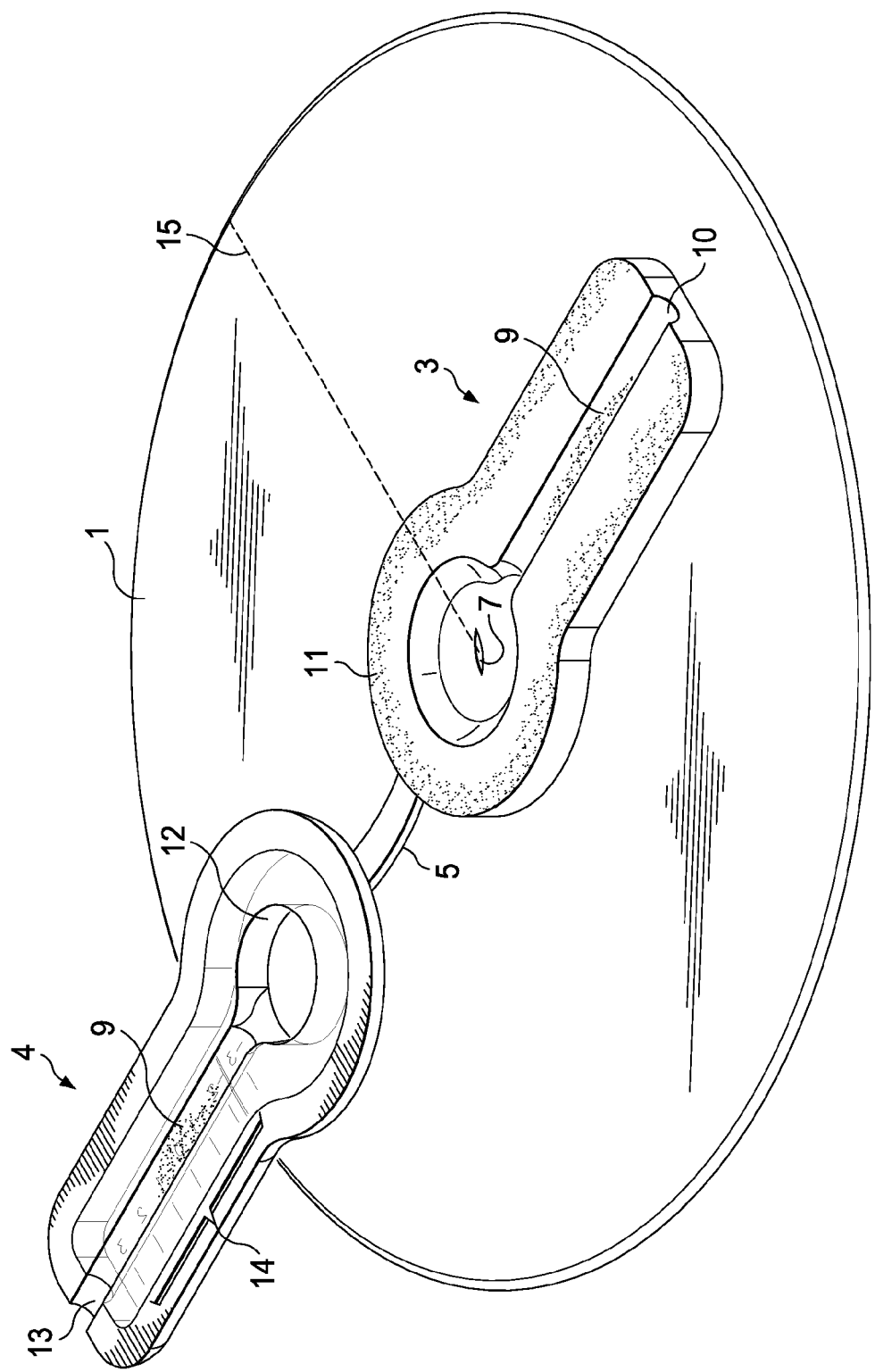
FIG. 3 illustrates various components of the foundation and the cover of the device in accordance with various embodiments.
Figure 4:
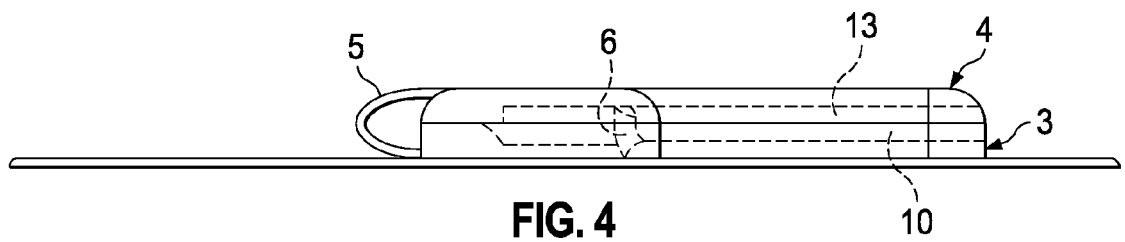
FIG. 4 illustrates a side view of the device in accordance with various embodiments.

Reference is made to FIGS. 1-4, which show various views of the device in accordance with various embodiments. FIG. 1 shows a top view of the device, while FIG. 2 shows a bottom view of the device. FIG. 3 illustrates various components of the foundation and the cover of the device, while FIG. 4 illustrates a side view of the device in accordance with various embodiments. As shown in FIG. 1, the device includes various structural elements, including a film 1, which is impregnated with an antimicrobial substance and large enough to cover the insertion site.

The device further comprises indicators 2 (e.g., indicators disposed in millimeter increments) to alert healthcare providers of any catheter positional shifts, which may be hazardous to the patient. The device further comprises a catheter securement foundation 3, a catheter securement cover 4, and a catheter securement hinge 5, each of which may be made from clear medical grade silicone, for example. As shown, both the catheter securement foundation 3 and the catheter securement cover 4 include a circular portion and an elongated portion.

The device further comprises a tapered catheter guide entrance way 6 (FIG. 4), a catheter entry point 7 (FIG. 2), and a tapered edge 8 (FIG. 2) for the entry point, where the catheter entry point 7 through the device may comprise a catheter entry point that allows the catheter to enter the patient's skin. When embodied as a slit, the catheter entry point 7 is approximately the same size as the diameter of the catheter, thereby allowing the catheter to be threaded through the catheter entry point 7 upon insertion of the catheter into the patient. Thereafter, the device is attached to the skin, as described above.

With reference to FIG. 3, the device further comprises a securement foundation guide channel 10. An adhesive 11 (e.g., silicone adhesive) is provided to secure the catheter securement cover 4 to the catheter securement foundation 3. The device further comprises a recess 12 configured to provide the catheter with more room to enter the securement foundation guide channel portion 10. The device further comprises a catheter securement cover guide channel portion 13. A medical grade adhesive 9 such as with antimicrobial properties is disposed on the securement cover guide channel portion 13 to restrict movement of the catheter.

Medical grade adhesive may also be disposed on the securement foundation guide channel portion 10. With reference to FIG. 4, when the hinge 5 is placed in a closed state, the securement cover guide channel portion 13 and the securement foundation guide channel portion 10 form an enclosed guide channel that secures the catheter. The diameter of the guide channel formed by the guide channel portions 10, 13 will vary depending on the diameter of the catheter line being inserted into the patient. The device further comprises catheter positional shift alert media 14 and an opening 15 in the catheter securement foundation 3 and the film.

Having briefly described the various structural components of the device, the construction of the device and corresponding components are now described. With reference back to FIG. 3, the catheter securement foundation 3 is contiguous with the antimicrobial film 1, where the opening 15 allows the device to encompass the catheter. The medical grade adhesive 9 with antimicrobial substances is disposed on the bottom side of the film 1, which positions and secures the device onto the patient's skin. The adhesive 9 is also disposed on the foundation guide channel portion 10 and cover guide channel portion 13 to secure the catheter to the device and prevent unwanted positional shifts by the catheter. Note that while FIG. 3 shows the adhesive 9 being disposed on only a portion of the foundation guide channel portion 10 and cover guide channel portion 13, the adhesive 9 may be disposed along the entire of length of these members.

The catheter entrance hole 7, tapered edge 8 (FIG. 2), recess 12, and the tapered catheter guide entrance 6 (FIG. 4) are all molded into the device. The catheter securement hinge 5 couples the catheter securement foundation 3 to the securement cover 4. The securement foundation guide channel 10 and the catheter securement cover guide channel 13 are molded into the securement foundation 3 and the securement cover 4, respectively. When the catheter securement foundation 3 and the securement cover 4 are placed in a closed state via the hinge 5 as shown in FIG. 4, the securement foundation guide channel 10 and the catheter securement cover guide channel 13 form a guide channel for the catheter. For some embodiments, the guide channel has a diameter that is approximately the same diameter of the catheter.

For some embodiments, a silicone adhesive 11 is disposed on the top of the catheter securement foundation 3 to secure the securement cover 4 onto the securement foundation 3 once the securement cover 4 and the securement foundation 3 are placed in a closed state via the hinge 5. A catheter positional shift alert media 14 is constructed in the securement cover 4, where indicators 2 with millimeter increments are etched into the catheter securement cover 4. For some embodiments, the opening 15 is cut as a final step of the manufacturing process into the catheter securement foundation 3 and film 1. Note, however, that the opening 15 is optional and that the catheter may be alternatively threaded through the catheter entry point 7 upon insertion into the patient. For some embodiments, the device may include both an opening 15 and a catheter entry point 7. In other embodiments, the device may include only an opening 15.

The film 1, medical grade adhesive 9, and the antimicrobial substance disposed on the medical grade adhesive 9 operate in conjunction to secure the device to the patient's skin and to prevent infections. The catheter is secured by the guide channel portions 10, 13 in the foundation 3 and securement cover 4 through the use of one or more adhesives 9 impregnated with antimicrobial substances. This allows the position of the catheter to be restricted, thereby preventing any unintended positional shifts and infections. The catheter position alert media 14 in conjunction with the millimeter increment indicators 2 are configured to alert health care providers of any unintentional positional changes.

For various embodiments, the device may be constructed via injection molding using medical grade silicone. Silicone adhesives may be used to join the catheter securement foundation 3 with the film 1. One or more medical grade adhesives 9 impregnated with antimicrobial substances are applied to the bottom of the film 1. During production, a removable preservative wax film is also applied to the areas where adhesives are disposed. The catheter positional shift alert media 14 is constructed into the securement cover 4 and comprises a positional indicator 16 fixedly attached to the catheter for purposes of alerting healthcare provides of any movement by the catheter. The positional indicator 16 may be composed of different substances in various embodiments. Some examples include, but are not limited to, a colored band of adhesive, a colored silicone band, or a colored dye integrated into the adhesive. Finally, a removable preservative film is applied to the mating surfaces of the securement cover 4 and the foundation 3. Upon production, the device is sterilized and packed in sterile fashion prior to usage.

The device may be constructed using medical grade silicone rubbers, plastics, fabrics, or other suitable materials. The type of antimicrobial substance used in the device may also be varied to address specific microorganisms or conditions. It should be noted that the dimensions and orientation of individual or assembled components may be varied for use with different types of medical catheters. Similarly the positional alert media 14 and the corresponding components (positional indicator 16, proximal alert zone 18, and distal alert zone 19) can be altered to adapt to different types of catheters. Additionally, certain aspects of individual components can potentially be altered to meet dimensional or environmental conditions present during the usage of the medical catheter.

Upon sterile placement of a medical catheter into a patient, the device is removed from the sterile packaging and loaded in sterile fashion around the entrance site of the catheter onto the patient's skin. During securement of the catheter by the device, the catheter body is placed in optimal position of the device by utilizing the opening 15 in the film 1 and the guide channel portions 10, 13 present in the securement foundation 3 and the cover 4, respectively. Once optimal position has been achieved, the film 1 of the device is adhered onto the skin of the patient. The device is then closed around the body of the catheter by adhering the foundation 3 and securement cover 4 together. This allows for securement and prevention of dangerous positional shifts. During the lifetime usage of the medical catheter, healthcare providers can assess and be alerted to changes in catheter position by utilizing the millimeter indicators 2 and positional alert media 14.

Figure 5:
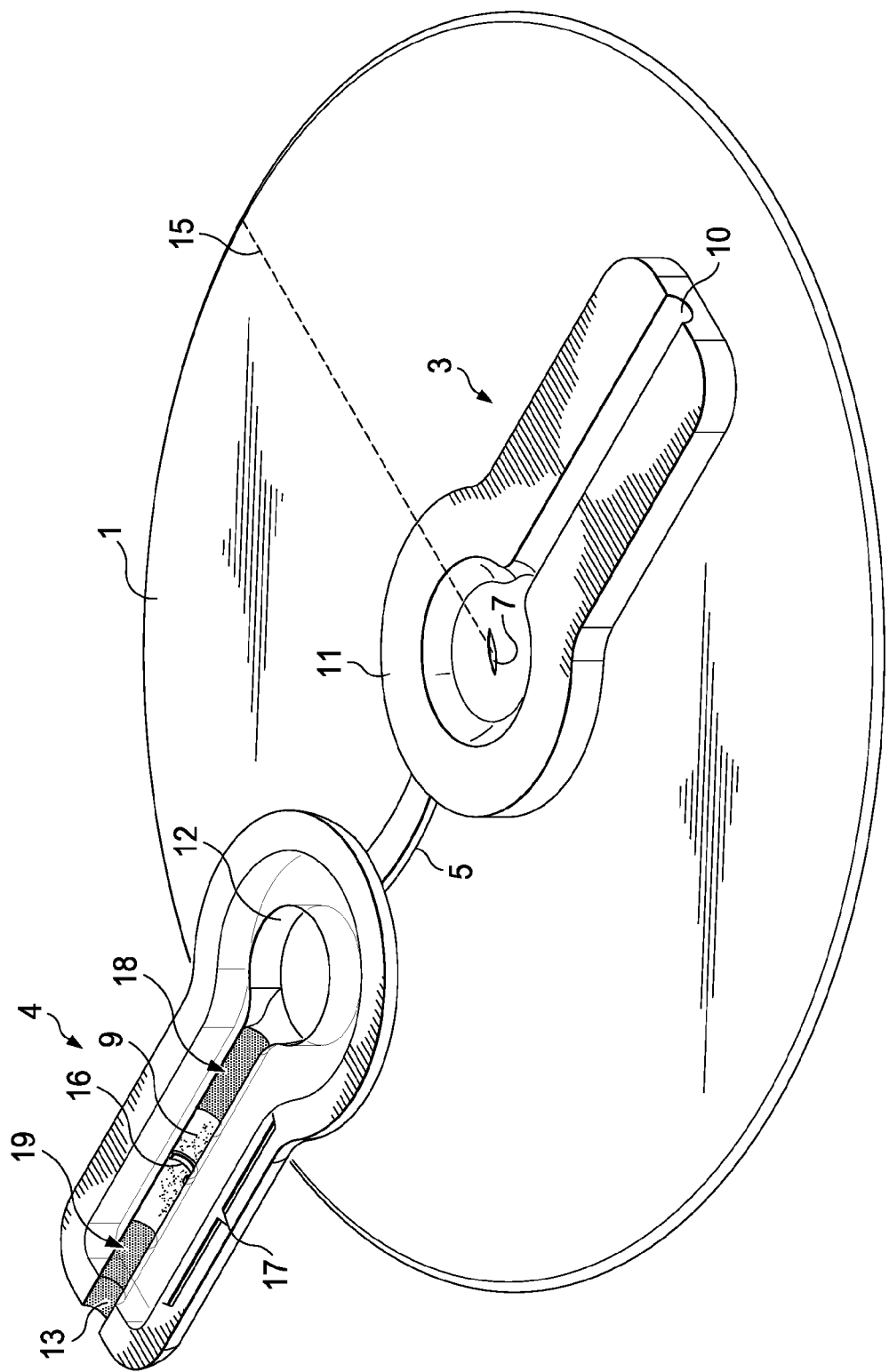
FIG. 5 is a detailed view of the catheter positional shift alert media and the indicators with millimeter increments in accordance with various embodiments.

Reference is made to FIG. 5, which provides a detailed view of the catheter positional shift alert media 14 in accordance with various embodiments, where the positional shift alert media 14 comprises a positional indicator 16 embedded in a medical grade adhesive 9. Prior to insertion of the catheter into the securement device, the positional indicator 16 may be initially disposed in the cover guide channel 13 and specifically, in the center of the clear transparent window 17.

Once the catheter is placed in the foundation guide channel portion 10, the securement hinge 5 is used to place the foundation 3 and securement cover 4 in a closed state, and the medical grade adhesive 9 fixedly attaches the positional indicator 16 to the catheter. Thereafter, any movement by the catheter will cause the positional indicator 16 in the positional alert media 14 to shift accordingly due to placement of the medical grade adhesive 9 in the cover guide channel 13. The positional alert media 14 therefore allows healthcare providers to detect inward or outward shifts in catheter position. The positional alert media 14 is constructed within the catheter securement cover guide channel 13. In addition to the positional indicator 16 and the medical grade adhesive 9, the positional alert media 14 further comprises a clear transparent window 17, a proximal positional alert zone 18, and a distal positional alert zone 19.

The proximal positional alert zone 18 and the distal positional alert zone 19 within the transparent window 17 may comprise tinted regions in the securement cover 4, where the tinted regions may be the same or different colors. Specifically, the proximal positional alert zone 18 and the distal positional alert zone 19 are tinted such that healthcare providers can view the location of the positional indicator 16 within each alert zone, as shown, for example, in the top views provided in FIGS. 10 and 11.

Figure 12:
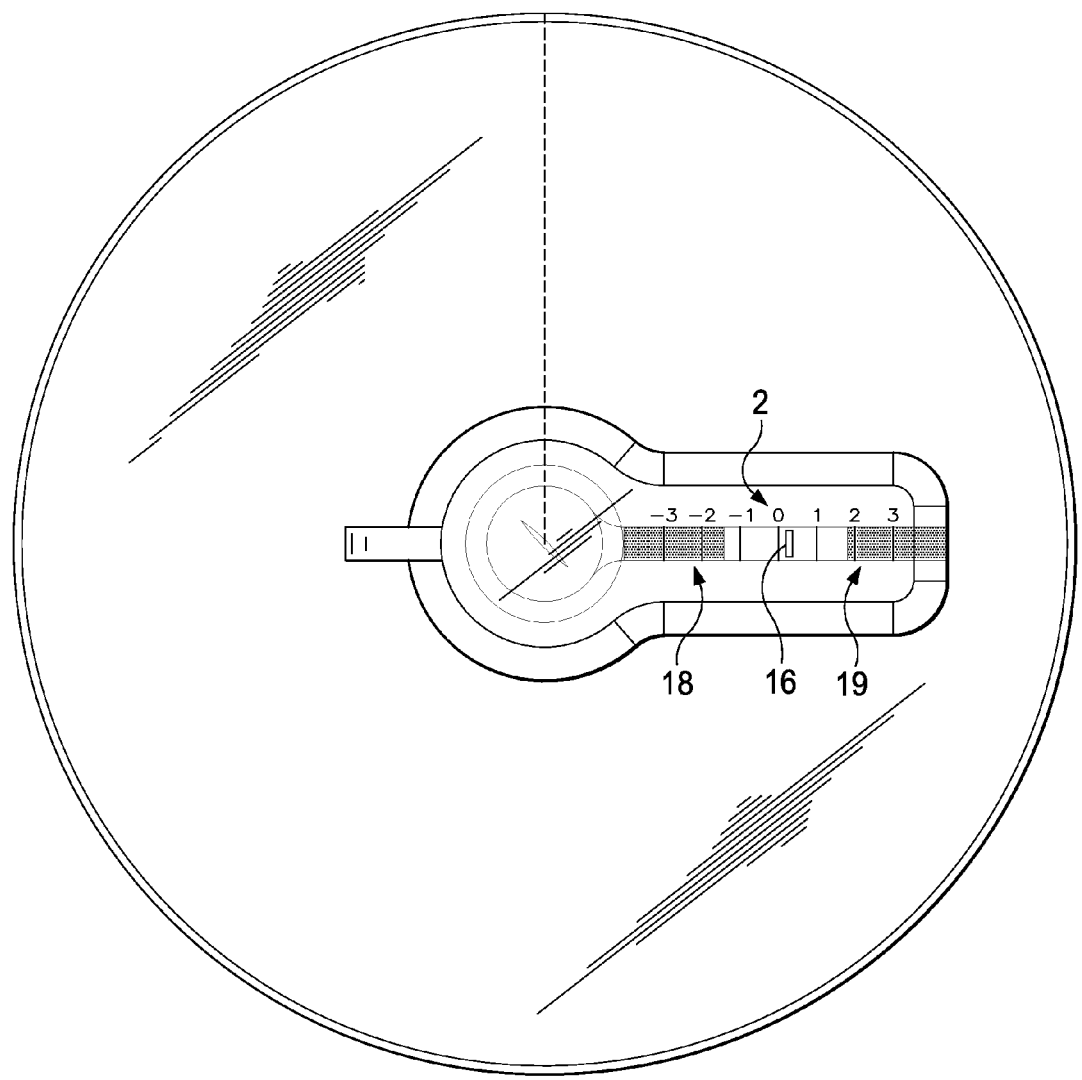
FIG. 12 illustrates a catheter securement cover guide channel that includes millimeter indicators and positional alert zones in accordance with various embodiments.

Referring back to FIG. 1, the indicators 2 with millimeter increments may be implemented as an alternative or in combination with the proximal positional alert zone 18 and the distal positional alert zone 19 of FIG. 5. For example, FIG. 12 is an embodiment where the catheter securement cover guide channel includes indicators 2, a proximal positional alert zone 18, and a distal positional alert zone 19 used in conjunction with a positional indicator 16. For the embodiment shown in FIG. 1, the indicator 2 are etched into the clear transparent window 17 (FIG. 5) such that the indicators 2 remain static relative to the catheter securement cover guide channel 13. Thus, any movement by the catheter and the attached positional indicator 16 will alert healthcare providers that catheter has shifted. Furthermore, the indicators 2 provide a measure of how far and in which direction the catheter has shifted.

Figure 6:
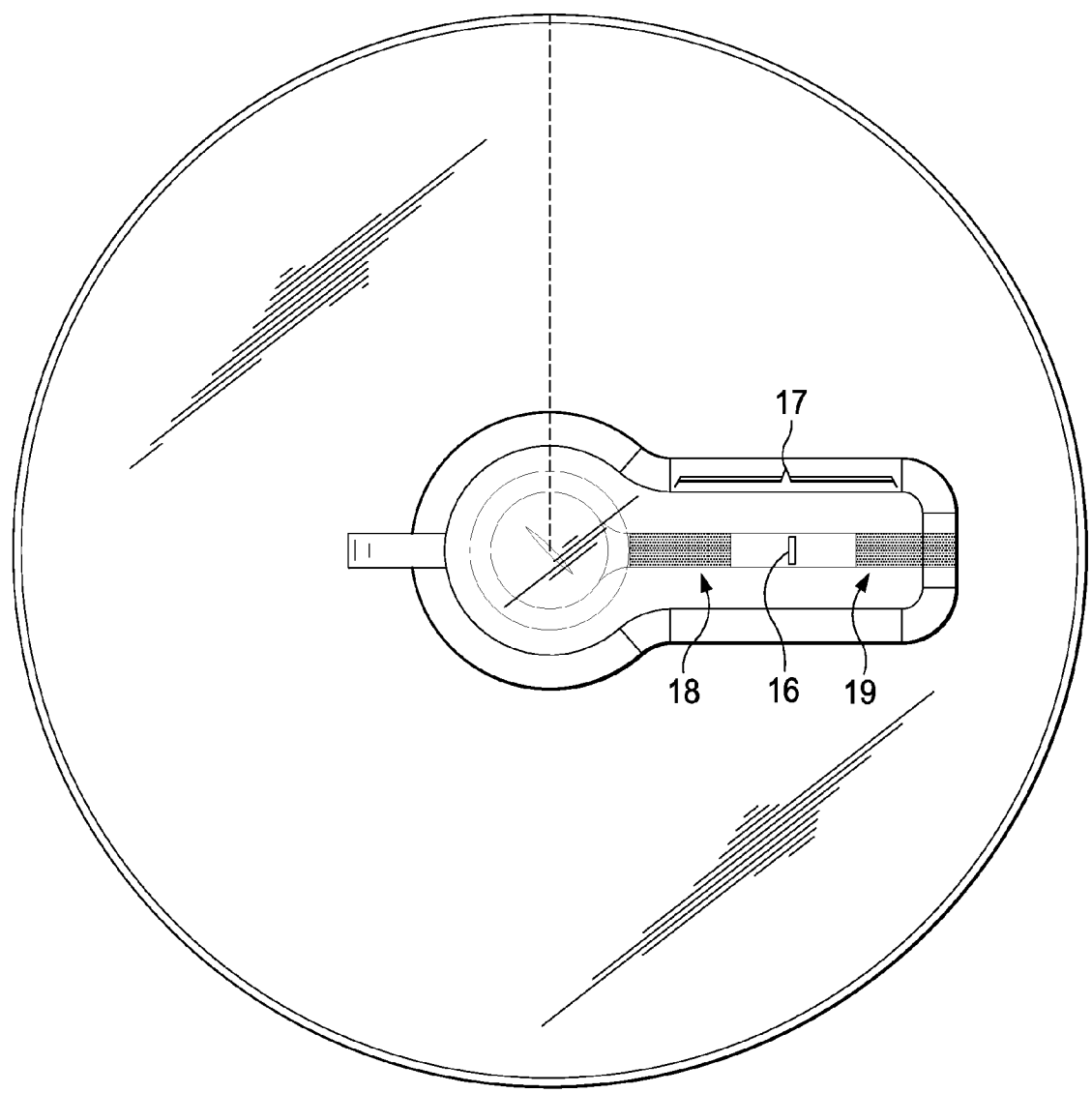
FIG. 6 illustrates the device in a closed configuration whereby the foundation is adhered to the securement cover in accordance with various embodiments.

FIG. 6 illustrates the device in a closed configuration whereby the foundation 3 is adhered to the securement cover 4. The proximal positional alert zone 18 and distal positional alert zone 19 are integrated into the clear transparent window 17. The components described above operate in conjunction in order to alert health care providers of dangerous inward or outward shifts of the medical catheter. The positional indicator 16 is applied to the catheter once the catheter is in the correct position during the initial loading process and secured to the foundation 3. Once the catheter has been securely loaded within the device, a healthcare provider is able to easily visualize the medical catheter, the positional indicator 16, and its relative position within the device. As shown, when the positional indicator 16 is initially attached to the catheter via the medical grade adhesive 9 (FIG. 5), the positional indicator 16 is centrally located between the proximal positional alert zone 18 and the distal positional alert zone 19.

Figure 7:
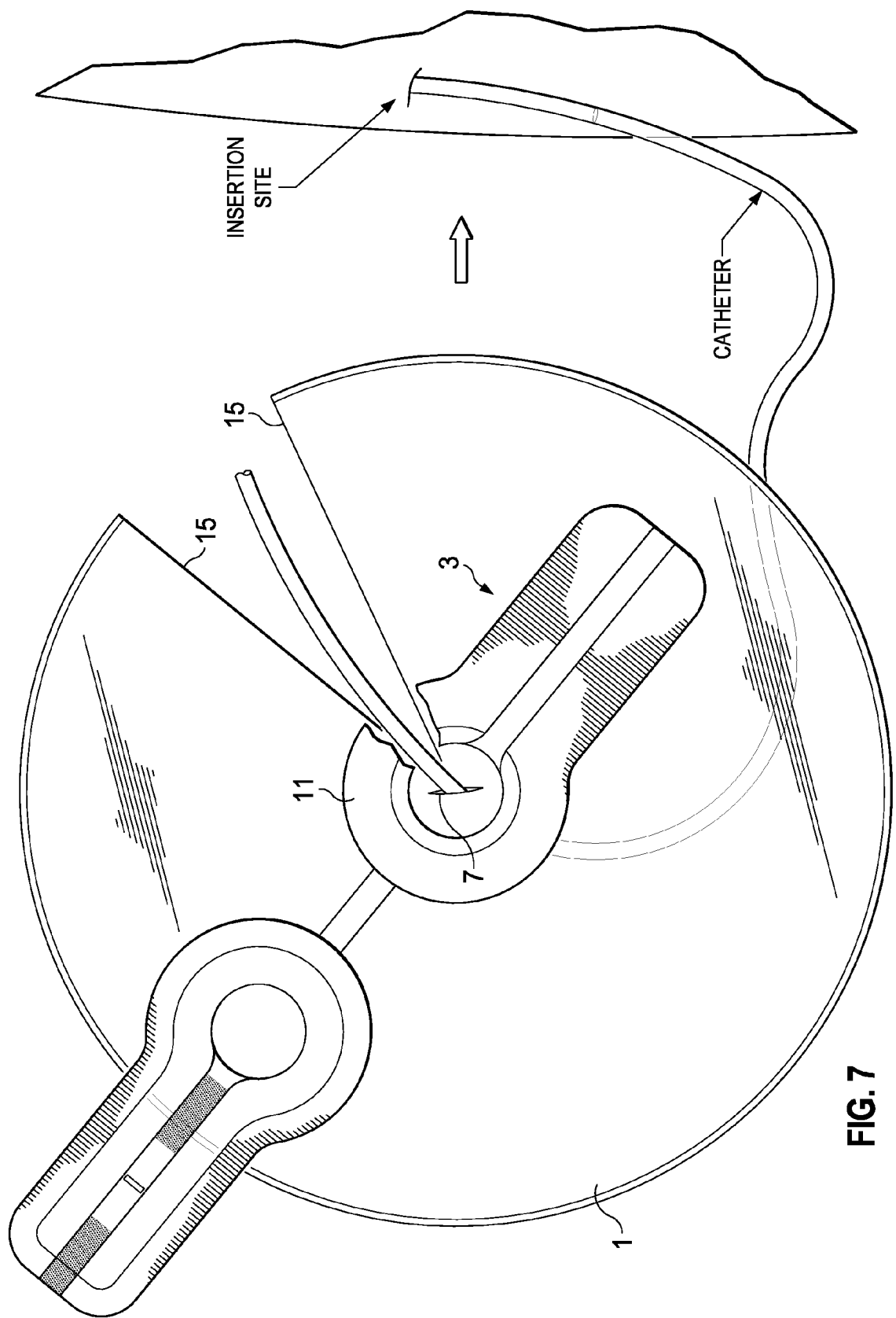
FIG. 7 illustrates the catheter exiting the patient's arm with the device being loaded around catheter through the opening in the device.
Figure 8:
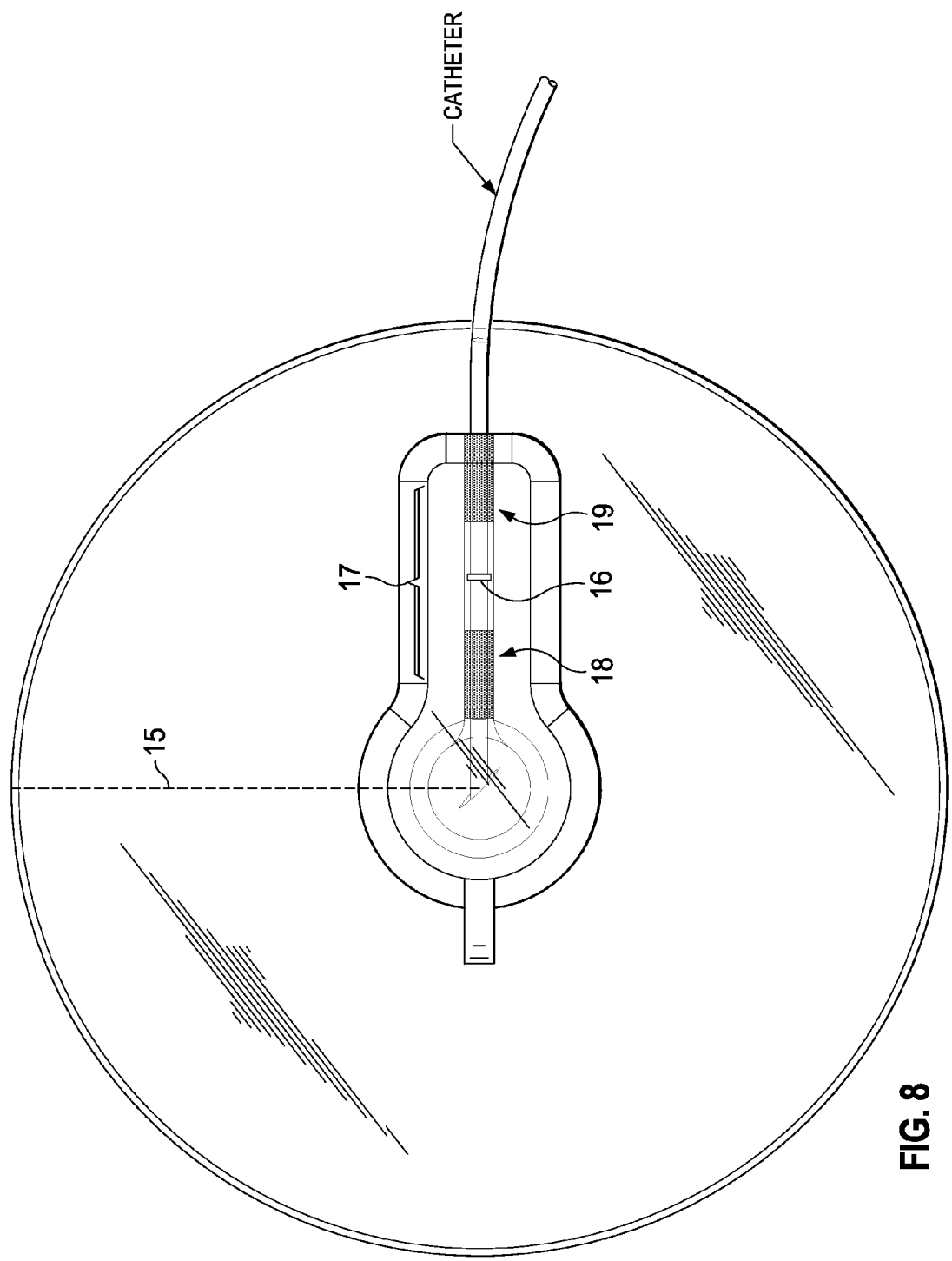
FIG. 8 illustrates placement of the catheter within the foundation, with the positional indicator reflecting optimal positioning of the catheter.
Figure 9:
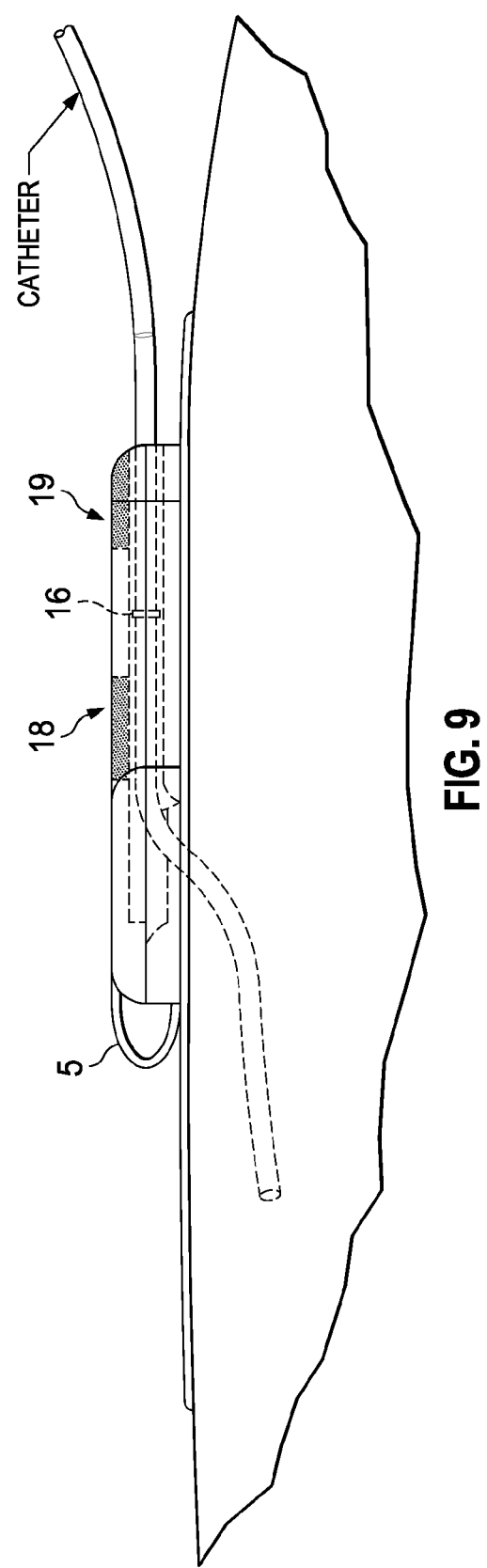
FIG. 9 is a lateral view of the device loaded around the catheter in optimal position.

FIG. 7 illustrates the catheter exiting the patient's skin with the device being loaded around catheter through the opening 15 in the device. For alternative embodiments, the device may be constructed without the opening 15, and the catheter may be threaded through the catheter entry point 7 (FIG. 2) upon insertion into the patient. FIG. 8 illustrates placement of the catheter being secured by the device, with the positional indicator 16 reflecting optimal positioning of the catheter. FIG. 9 is a lateral view of the device loaded around the catheter in optimal position.

Figure 10:
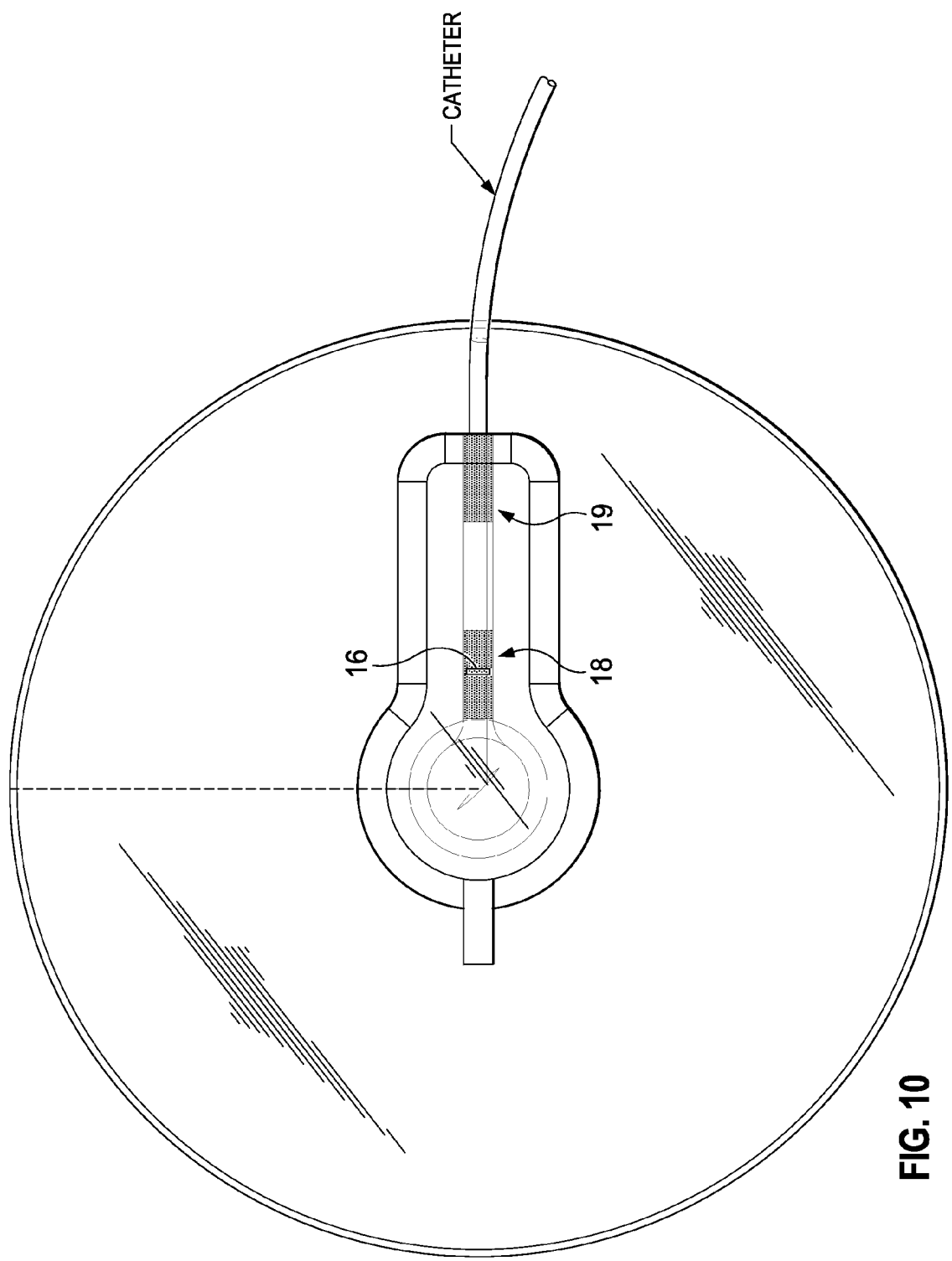
FIG. 10 is a top view of the device loaded around catheter, where the positional indicator reflects an inward shift of the catheter.
Figure 11:
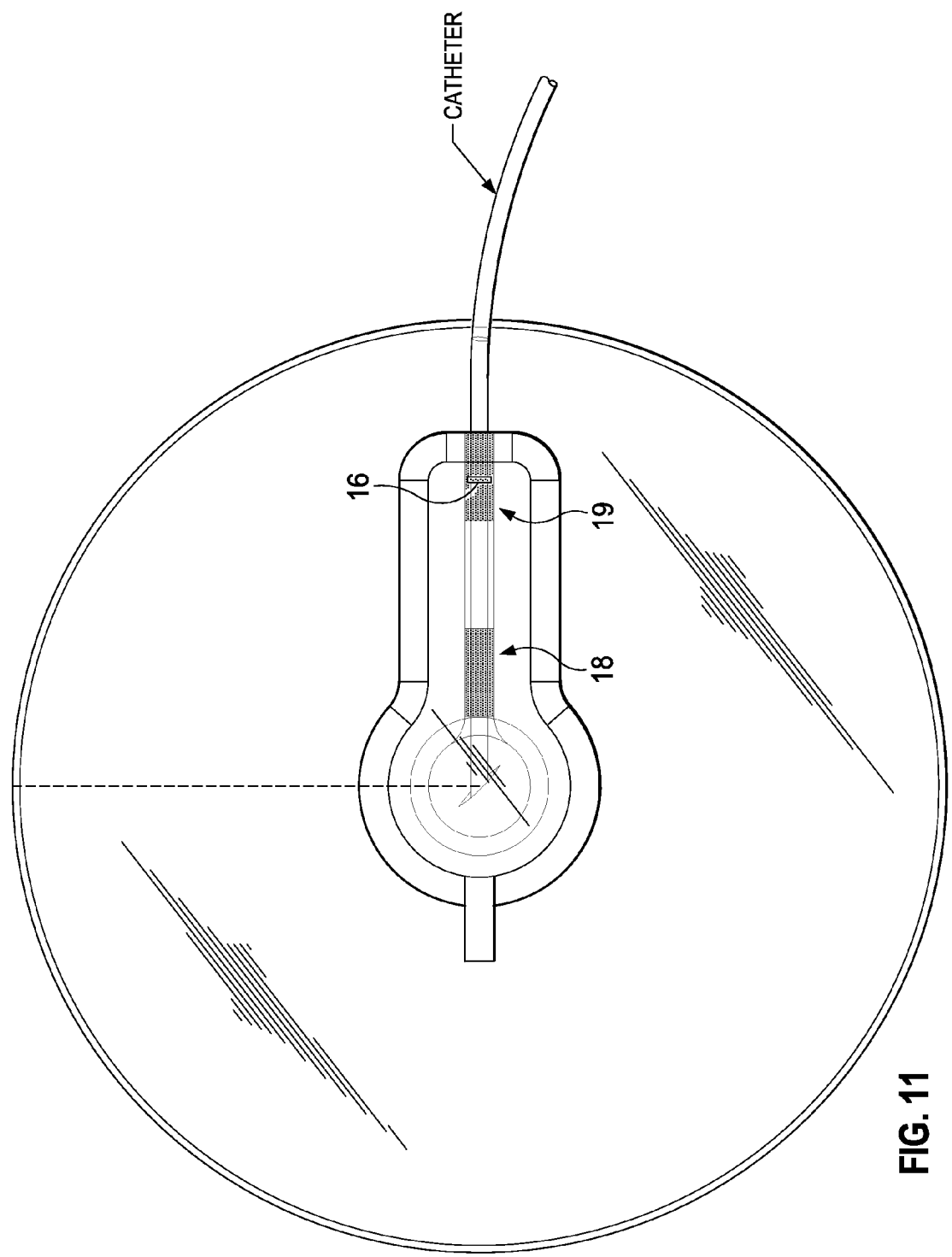
FIG. 11 is a top view of the device loaded around the catheter, where the positional indicator reflects an outward shift of the catheter.

FIG. 10 is a top view of the device loaded around catheter, where the positional indicator 16 reflects an inward shift of the catheter, while FIG. 11 is a top view of the device loaded around the catheter, where the positional indicator 16 reflects an outward shift of the catheter. In this regard, the two alert zones 18, 19 serve as reference points that indicate the direction in which the catheter has shifted. Specifically, if the positional indicator 16 moves within the proximal alert zone 18 shown, this alerts the healthcare provider that the catheter has moved inwards towards the entry site. Similarly, if the positional indicator 16 is within the distal alert zone 19, this alerts the healthcare provider that the catheter has moved outward from the entry site.

Note that while only a single positional indicator 16 is shown, multiple embodiments of positional indicators 16 and millimeter indicators 2 may be used to convey how far the catheter has shifted within the cover guide channel 13. Note that while only a single positional indicator 16 is shown, multiple positional indicators 16 may be utilized to convey how far the catheter has shifted within the cover guide channel 13. The catheter positional shift alert media 14 is disposed within the top of the securement cover 4. A positional indicator 16 is attached to the catheter during installation and is easily viewed within the clear transparent window 17.

The positional indicator 16 may comprise a half-ring member constructed of plastic or other suitable material, where the positional indicator 16 is embedded within the medical grade adhesive 9 (FIG. 5) disposed in the cover guide channel 13 (FIG. 5). Alternatively, the positional indicator 16 may be comprise a line indicator constructed of dye embedded within the medical grade adhesive 9. Through the medical grade adhesive 9, the positional indicator 16 is fixedly attached to the catheter when the foundation 3 and the securement cover 4 are placed in a closed position via the securement hinge 5.

It should be emphasized that the above-described embodiments are merely examples of possible implementations. Many variations and modifications may be made to the above-described embodiments without departing from the principles of the present disclosure.

The invention claimed is:

1. A device for securing and monitoring movement of a medical catheter, comprising:
    a film having an adhesive disposed on a body-facing surface for securing the film to a body, the adhesive having antimicrobial properties;
    a securement foundation mounted on the film;
    a securement cover; and
    a hinge member coupling the securement foundation to the securement cover, wherein when the securement cover and the securement foundation are configured in a closed state via the hinge, the securement cover and the securement foundation form a housing with a guide channel for securing the catheter,
    wherein an adhesive is disposed on a surface of the guide channel for restricting movement of the catheter within the housing formed by the securement cover and the securement foundation,
    wherein the securement cover further comprises positional shift alert media configured to indicate positional shifts by the catheter relative to the housing,
    wherein the position shift alert media comprises a positional indicator embedded in the adhesive disposed on the surface of the guide channel, wherein when the securement cover and the securement foundation are configured in the closed state, the positional indicator is fixedly attached to the catheter via the adhesive,
    wherein the securement cover is constructed of a clear medical grade silicone material, and
    wherein the positional shift alert media further comprises a plurality of tinted regions in the securement cover, the tinted regions being located at a distal end and at the proximal end of the securement cover, wherein the positional indicator fixedly attached to the catheter is viewable from a top view through a top surface of the securement cover, and wherein the positional indicator fixedly attached to the catheter is initially centrally located relative to the tinted regions.

2. A device for securing and monitoring movement of a medical catheter, comprising:
    a film having an adhesive disposed on a body-facing surface for securing the film to a body, the adhesive having antimicrobial properties;
    a securement foundation mounted on the film;
    a securement cover; and
    a hinge member coupling the securement foundation to the securement cover, wherein when the securement cover and the securement foundation are configured in a closed state via the hinge, the securement cover and the securement foundation form a housing with a guide channel for securing the catheter,
    wherein an adhesive is disposed on a surface of the guide channel for restricting movement of the catheter within the housing formed by the securement cover and the securement foundation,
    wherein the securement cover further comprises positional shift alert media configured to indicate positional shifts by the catheter relative to the housing,
    wherein the position shift alert media comprises a positional indicator embedded in the adhesive disposed on the surface of the guide channel, wherein when the securement cover and the securement foundation are configured in the closed state, the positional indicator is fixedly attached to the catheter via the adhesive,
    wherein the securement cover is constructed of a clear medical grade silicone material, and wherein the positional shift alert media further comprises a plurality of line indicators etched into the securement cover, wherein the positional indicator fixedly attached to the catheter is viewable from a top view through a top surface of the securement cover.

3. The device of claim 2, wherein in the closed state, the securement cover and the securement foundation further comprise a recess at a proximal end of the housing for insertion of the catheter into the body.

4. The device of claim 3, wherein a region in which the recess overlays the film comprises a catheter entry point for insertion of the catheter into the body, wherein the securement foundation is aligned with the catheter entry point such that the catheter protruding from the body enters through the catheter entry point of the film into the recess and enters the guide channel.

5. The device of claim 2, wherein the line indicators are spaced 1 mm apart.

6. A method for securing and monitoring movement by a medical catheter, comprising:
    inserting the medical catheter into the body; threading the medical catheter through a catheter entry point in a film having an adhesive disposed on a body-facing surface, the adhesive having antimicrobial properties;
    attaching the film to the body via the adhesive;
    placing the catheter in a guide channel formed by a securement foundation and a securement cover, the securement foundation being mounted on the film, and the securement foundation being coupled to the securement cover via a hinge;
    placing the securement foundation mounted and the securement cover in a closed state via the hinge to form a housing around the catheter, wherein an adhesive disposed on a surface of the guide channel restricts movement of the catheter within the housing, wherein the securement cover further comprises positional shift alert media configured to indicate positional shifts by the catheter relative to the housing, wherein the position shift alert media comprises a positional indicator embedded in the adhesive applied to the surface of the guide channel, wherein when the securement cover and the securement foundation are configured in the closed state, the positional indicator is fixedly attached to the catheter via the adhesive, and wherein the securement cover is constructed of a clear medical grade silicone material, and wherein the positional shift alert media further comprises a plurality of tinted regions in the securement cover, wherein the positional indicator fixedly attached to the catheter is viewable from a top view through a top surface of the securement cover.

7. The method of claim 6, further comprising monitoring movement of the positional indicator relative to the plurality of tinted regions in the securement cover.

8. The method of claim 7, further comprising determining, based on a location of the positional indicator in one of the plurality of tinted regions, a direction of movement by the medical catheter.

9. A device for securing and monitoring movement of a medical catheter, comprising:
- a film having an adhesive disposed on a body-facing surface for securing the film to a body, the adhesive having antimicrobial properties;
- a securement foundation mounted on the film;
- a securement cover, wherein both the securement foundation and the securement cover comprise a circular portion and an elongated portion; and
- a hinge member coupling the securement foundation to the securement cover, wherein when the securement cover and the securement foundation are configured in a closed state via the hinge, the securement cover and the securement foundation form a housing with a guide channel within the elongated portion for securing the catheter, the guide channel having approximately a same diameter as a diameter of the medical catheter, the guide channel having an adhesive disposed thereon for restricting movement of the medical catheter, wherein the film comprises a catheter entry point for insertion of the catheter into the body, and wherein the circular portion of the securement foundation is aligned with the catheter entry point such that the catheter protruding from the body enters through the catheter entry point of the film and enters the guide channel, wherein the securement cover further comprises positional shift alert media configured to indicate positional shifts by the catheter relative to the housing, wherein the position shift alert media comprises a positional indicator embedded in the adhesive disposed on the surface of the guide channel, wherein when the securement cover and the securement foundation are configured in the closed state, the positional indicator is fixedly attached to the catheter via the adhesive, and wherein the securement cover is constructed of a clear medical grade silicone material, and wherein the positional shift alert media further comprises a plurality of tinted regions in the securement cover, wherein the positional indicator fixedly attached to the catheter is viewable from a top view through a top surface of the securement cover.

* * * * *